(12) United States Patent
Grove et al.

(10) Patent No.: US 7,299,709 B1
(45) Date of Patent: Nov. 27, 2007

(54) AEROSOL COLLECTING DEVICE FOR A CHEMICAL DETECTOR

(75) Inventors: Corey M. Grove, Red Lion, PA (US); Stephen E. Chase, Jarrettsville, MD (US); Thomas F. Mitchell, Edgewood, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/355,790

(22) Filed: Feb. 16, 2006

(51) Int. Cl.
*G01N 1/00* (2006.01)
(52) U.S. Cl. .................................................. 73/863.11
(58) Field of Classification Search ............... 73/863.11
See application file for complete search history.

(56) References Cited

U.S. PATENT DOCUMENTS

| | | | | |
|---|---|---|---|---|
| 5,123,274 A | * | 6/1992 | Carroll et al. ........... | 73/863.12 |
| 5,904,900 A | * | 5/1999 | Bleuse et al. ................. | 422/99 |
| 6,192,766 B1 | * | 2/2001 | Gårdhagen et al. ...... | 73/863.12 |
| 2001/0042413 A1 | * | 11/2001 | Sakairi et al. ........... | 73/863.11 |
| 2006/0081073 A1 | * | 4/2006 | Vandrish et al. ......... | 73/864.33 |
| 2007/0034024 A1 | * | 2/2007 | Syage ..................... | 73/863.12 |

* cited by examiner

*Primary Examiner*—Robert Raevis
(74) *Attorney, Agent, or Firm*—Ulysses John Biffoni

(57) ABSTRACT

An aerosol collecting device adapted for attachment to a chemical vapor detection system is disclosed to include a chamber comprising an inlet with a collecting funnel attached thereto and open to ambient, an outlet, and a through cavity defined therebetween, wherein the outlet is adapted for fluid connection with an input port of the chemical vapor detection system; and a heating element for heating the chamber to a temperature above the boiling point of a target chemical agent of interest in the form of a droplet or aerosol, wherein the chemical agent in the form of a droplet or aerosol is converted into a vapor form as it passes through the cavity from the inlet to the outlet of the chamber, and prior to entering the intake port of the chemical vapor detection system.

11 Claims, 5 Drawing Sheets

AEROSOL COLLECTING DEVICE FOR A CHEMICAL DETECTOR

GOVERNMENT INTEREST

The invention described herein may be manufactured, used and licensed by or for the U.S. Government.

FIELD OF THE INVENTION

The present invention relates to chemical detection and alarm systems, and more particularly to an aerosol collecting device adapted for enhancing and extending the detecting capability of chemical detection and alarm systems.

BACKGROUND OF THE INVENTION

The use of chemical warfare agents continues to be a viable threat to civilian populations as well as to military installations. Such chemical warfare agents possess toxic properties capable of killing, injuring or incapacitating people. It has been estimated that 25-27 nations possess chemical weapons, which are often referred to as the "poor man's nuclear weapon." The manufacture of chemical warfare agents in small quantities by terrorists is an ongoing threat, and the manufacture and use of military quantities of chemical warfare agents for delivery against U.S. troops is always a potential.

Therefore, effective countermeasures are needed to maintain adequate security and protection of population and military centers. Such countermeasures broadly include defense against chemical weapons and accurate means of detecting chemical agents. One type of a chemical agent detector means is a point detector capable of providing quick warning to those nearby that a chemical attack has occurred.

Chemical agents are colorless and sometimes odorless, which at very low concentrations, can cause incapacitation or more serious effects on people. Chemical warfare agents delivered to a target site may be in the form of a gas or vapor at room temperature that can affect the target through the lungs, skin and clothing, and are usually classified as non-persistent since they lose effectiveness after a few minutes or hours.

Other chemical warfare agents that are classified as persistent have a relatively high boiling point, and a relatively low vapor pressure. They are typically delivered to the target site in droplet forms, and can exhibit varying size droplet particles ranging from 100 microns to 5000 microns, depending on the delivery system used. The aerosolized delivery of such chemical warfare agents can be achieved even by low-tech aerosolization methods including agricultural crop-dusters, aerosol generators, backpack sprayers, or hand-size atomizers. Due to the properties of such agents, they tend to remain in the environment as a liquid for as long as a week. Thus, detection of such chemical warfare agents must be made at the earliest possible time to reduce the number of potential persons affected. Often, this is best facilitated through the detection of the agent in the droplet or aerosol form during the delivery phase.

Chemical vapor detection systems make up a class of point detectors that are reliable and effective in a range of testing conditions. They generally employ spectrometric techniques to identify compounds based on the unique spectral profile generated. The chemical vapor detection system separates and identifies each component of a molecule based on relative speeds of travel in an electric field.

The chemical vapor detection systems are efficient, relatively accurate and require no consumable testing materials or reagents. They can be used for continuous real time point sampling operations with minimal labor and maintenance requirements. Such systems can be left unattended in an area to monitor general air quality, or used to detect dangerous chemicals spreading in an area. Using such systems, chemical warfare agents in the form of vapors or gases can readily be detected, however, the same systems provide limited aerosol detection.

Liquid surface samplers can provide for aerosol detection if adequate aerosol deposition occurs on the tested surfaces. Such chemical detection systems are equipped to detect chemical agents in droplet or aerosol form, and operate by contact of the chemical agent to a detector plate in amounts sufficient to reach a saturation point. The detector plate includes a conducting circuit containing a chemically reactive conducting matrix. Once the agent comes in contact with the conducting matrix, the conducting matrix undergoes chemical changes, which activates the conducting circuit.

Such liquid surface sampling systems are less sensitive to chemical agents with very small droplet or aerosol particle sizes. Furthermore, such systems require regular replacement of the detector plate and maintenance, and depend on optimal testing conditions, while exhibiting slower reaction times and lower threshold of sensitivity than spectrometric methods.

Accordingly, there is a need for a device attachable to a chemical vapor detection system that can enhance its capability to monitor and detect droplet or aerosol forms of chemical warfare agents while enhancing the detection of vapor chemical agents, thus enabling detection of both vapor and droplet forms of chemical warfare agents over a range of temperatures and testing conditions in a simple, reliable and cost effective manner.

SUMMARY OF THE INVENTION

The present invention relates generally to an aerosol collecting device for a attachment to a chemical vapor detection system. The aerosol collecting device is designed to enhance the capability of chemical vapor detection systems that are generally limited to analyzing the vapor or gaseous form of a sample to screen for aerosolized chemical compounds of interest such as chemical warfare agents. The aerosol collecting device is modular and can be easily assembled and attached to existing systems, or constructed as part of a new system. The present invention reduces the cost, time and labor associated with monitoring and detecting compounds of interest and expanding the detection capability of the corresponding system in a simple, cost effective manner, while maintaining good accuracy, reliability and reproducibility.

In one aspect of the present invention, there is provided an aerosol collecting device adapted for attachment to a chemical vapor detection system, the collecting device comprising:

a chamber comprising an inlet open to ambient, an outlet, and a through cavity defined therebetween, the outlet being adapted for fluid connection with an input port of the chemical vapor detection system; and a heating element for heating the chamber to a temperature above the boiling point of a target chemical agent of interest in the form of a droplet or aerosol, wherein the chemical agent in the form of a droplet or aerosol is converted into a vapor form as it passes through the cavity from the inlet to the outlet of the chamber, and prior to entering the intake port of the chemical vapor detection system.

In another aspect of the present invention, there is provided a method for collecting a sample suspected of containing chemical agents for introduction to a chemical vapor detection system, the method comprising the steps of:

extracting the sample from ambient;

converting the aerosol or droplet forms of the chemical agents in the sample into a vapor or gas phase; and conveying the vapor or gas phase form of the chemical agents to the chemical vapor detection system.

BRIEF DESCRIPTION OF THE DRAWINGS

The following drawings are illustrative of embodiments of the present invention and are not intended to limit the invention as encompassed by the claims forming part of the application.

DETAILED DESCRIPTION OF THE INVENTION

The present invention is directed to an aerosol collecting device for attachment to a chemical detection system. In particular, the aerosol collecting device is designed to enhance the performance and capability of chemical vapor-based detection systems. The aerosol collecting device of the present invention ensures that chemical compounds in the form of droplets or aerosol particles are converted into a form compatible with chemical vapor detection systems. In this manner, the present invention operates to extend the detection capability and reliability of such chemical vapor detection systems. The aerosol collection device of the present invention provides an effective means for heating a fluid sample suspected of containing a chemical warfare agent above a pre-determined temperature to ensure the vaporization of the compounds of interest prior to testing by the chemical vapor detection system.

In one embodiment of the present invention, there is provided an aerosol collecting device adapted for attachment to a chemical vapor detection system, wherein the aerosol collecting device comprises a chamber comprising an inlet open to ambient, an outlet, and a through cavity defined therebetween, wherein the outlet is adapted for fluid connection with an input port of the chemical vapor detection system; and a heating element for heating the chamber to a temperature above the boiling point of a target chemical agent of interest in the form of a droplet or aerosol, wherein the chemical agent in the form of a droplet or aerosol is converted into a vapor form as it passes through the cavity from the inlet to the outlet of the chamber, and prior to entering the input port of the chemical vapor detection system.

Figure 1:
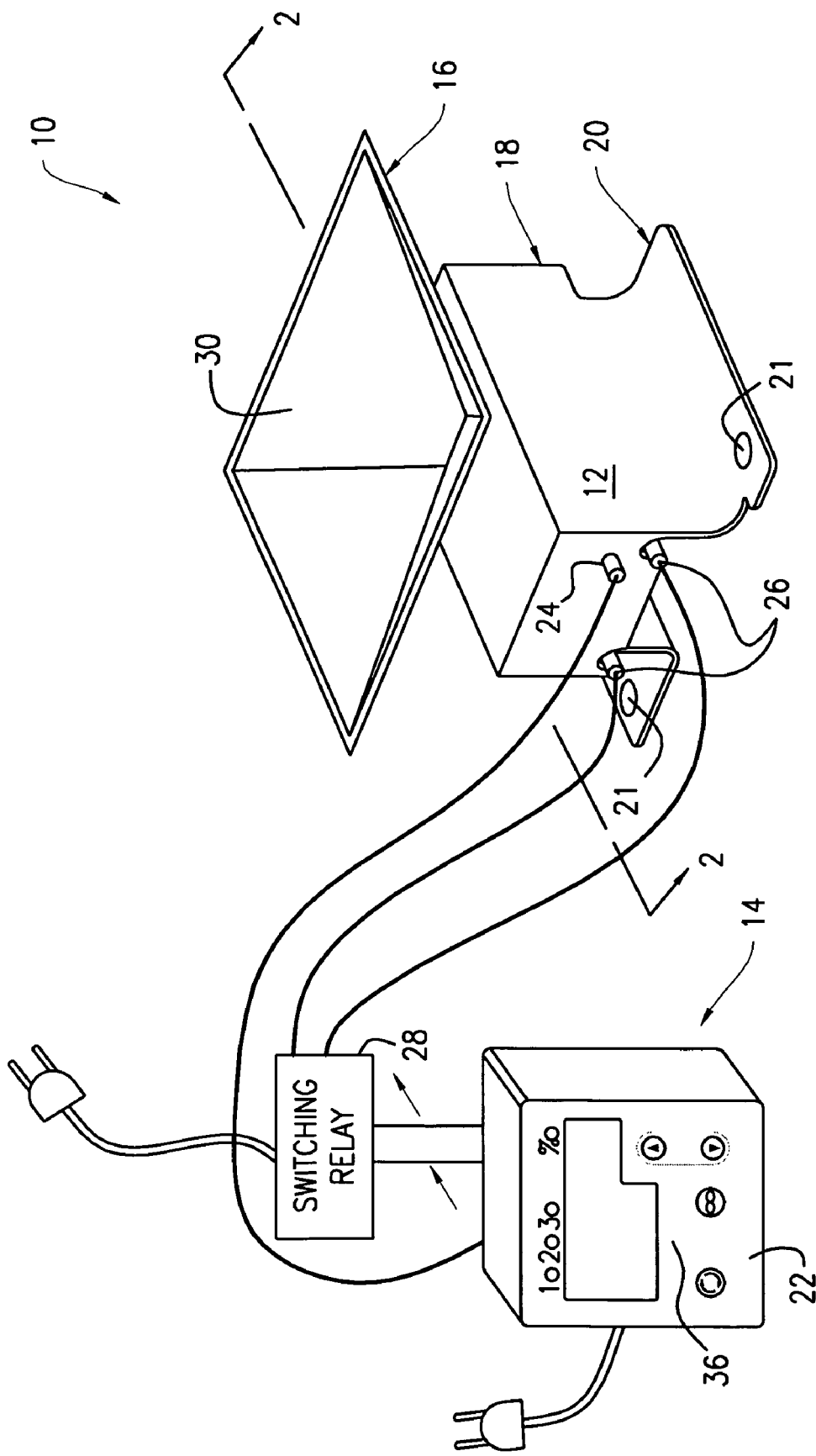
FIG. 1 is a perspective view of a chemical detector aerosol collector for one embodiment of the present invention.

Referring to FIG. 1, an aerosol collecting device identified generally by reference numeral 10 is shown for one embodiment of the present invention. The aerosol collecting device 10 can be readily assembled or constructed using commercially available off-the-shelf components. The aerosol collecting device 10 generally comprises a collecting component 12 and a heating component 14. The aerosol collecting device 10 is designed to fit on top of a chemical vapor detection system or the portion of the chemical detection system where the sample is admitted for testing such as, for example, an input port. The aerosol collecting device 10 facilitates collection of a fluid sample suspected of containing a chemical agent such as a chemical warfare agent, and uniformly processes the sample to ensure that the sample is in a form that maximizes the detection capability of the chemical vapor detection system.

The aerosol collecting device 10 is intended for operation in association with any chemical detection system utilizing vapor detection methods wherein the system is designed to analyze sample compounds primarily in the vapor or gaseous phase. One example of a suitable chemical detection system is the Advanced Chemical Agent Detection and Alarm System (ACADA), manufactured by Smiths Group of London, UK, which provides self-contained point detection of a range of chemical/biological agent vapors. The ACADA is an advanced man-portable, point sampling, chemical agent alarm system based on the use of ion mobile spectrometry (IMS) in which the vaporous agents in question are separated and identified by their relative speeds of travel (mobilities) in an electric field. The ACADA requires no liquid reagents, and is capable of detecting hazardous compounds in vapor form including all standard nerve, mustard, blister, and lewisite agents, and may be programmed to address other chemical compounds.

The ACADA and similar chemical detection systems typically include an input port for sampling the ambient air potentially containing vapor chemical agents for analysis, a testing component for analyzing the sample to the control unit acquired through the input port, and a reporting component to inform the user whether a compound of interest has been detected in the sample by the testing component. The aerosol collecting device 10 may be modified to be attached to the input port of any pre-existing chemical vapor detection systems.

The collecting component 12 includes a collection funnel 16 for maximizing the collection of a fluid sample suspected of containing chemical warfare agents, and a collection chamber housing 18 adapted for attachment to the chemical detection system via a mount 20. The mount 20 positions the device 10 at a fixed distance from the chemical detection system, and includes fastening holes 21 to allow the device 10 to be fixedly attached to the corresponding chemical detection system. The collecting component 12 can be composed of any suitable durable, chemically resistant material capable of withstanding a range of environmental conditions, temperatures and physical forces, and is preferably composed of a heat conducting material for facilitating rapid and uniform heating of the collection funnel 16 and the collection chamber housing 18 at a desired temperature range.

The heating component 14 includes a control unit 22 with a thermocouple 24, a pair of cartridge heaters 26 regulated through a switching relay 28 as will be further described hereinafter. The heating component 14 is assembled from parts available from commercial off-the-shelf products. The cartridge heaters 26 are available in varying diameters and lengths as need to meet the requirements of the device 10.

Two cartridge heaters 26 having 0.25-inch diameter, 2-inch long cartridges were utilized to test the device 10. Temperatures were easily adjusted from room temperature to several hundred degrees centigrade. The control unit 22, the switching relay 28 and thermocouple 24 are used to operate with the cartridge heaters 26 to ensure proper desired heating of the collecting component 18. The control unit 22 allows for temperature control throughout the range required to operate the device 10. The thermocouple 24 is used to relay temperature of the collection component 18 to allow the control unit 22 to switch the power to the cartridge heaters 26 as needed.

In one embodiment, the control unit 22 was a SERIES SD Controller Model No. SD6C-HCAA-AARG; the thermocouple was a thermocouple Model No. 20CJFD048A, the switching relay was a SSR series solid state relay Model No. SSR-240-25A-0C1, and the cartridge heaters were 0.25-inch diameter, 2-inch length, 120 volt, 150 watt, 24-inch standard lead, Product No. E2A56-24, each product marketed and sold by Watlow Electric Manufacturing Company of St. Louis, Mo. Alternatively, the separate heater and thermocouple may be replaced with a heater cartridge with a built-in thermocouple, which is 0.25-inch diameter, 2.75-inch length, 120 volt, 150 watt, Style B Type J thermocouple, 24-inch swaged teflon leads, Product No. E2N-9155, also marketed and sold by Watlow.

Figure 2:
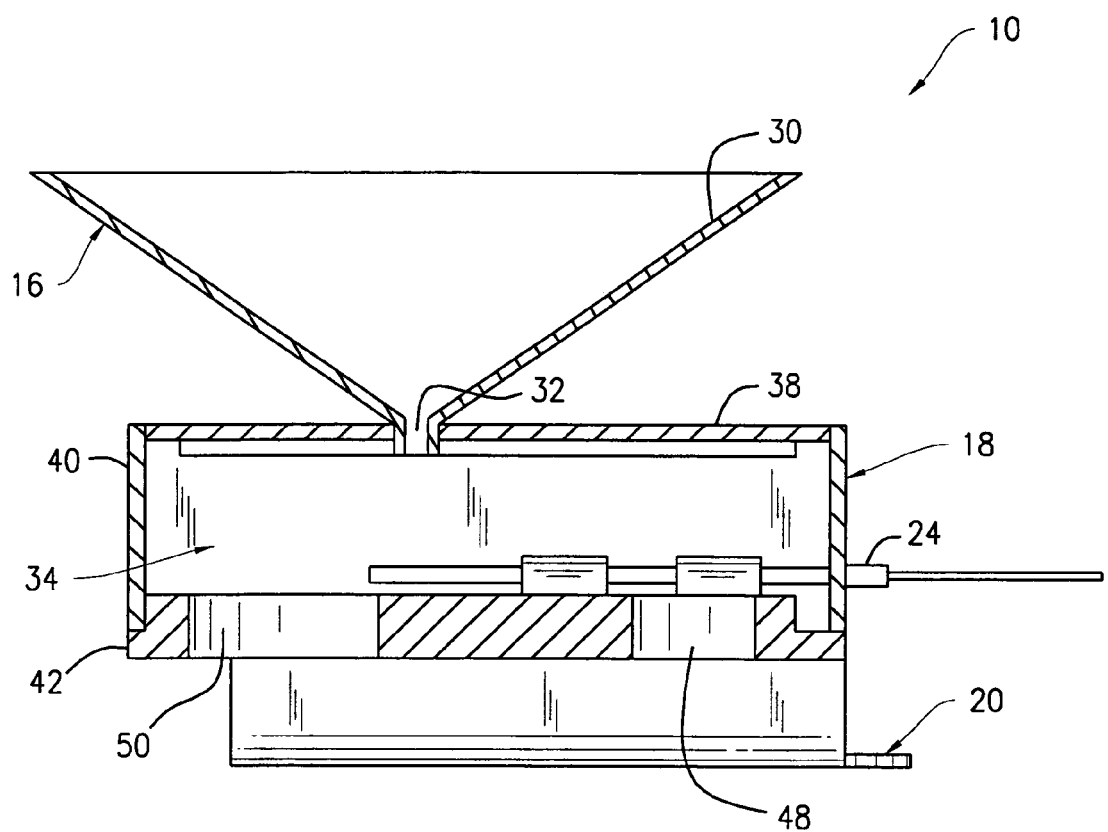
FIG. 2 is a cross sectional view of the chemical detector aerosol collector along lines 2-2 in accordance with the present invention.

The collector funnel 16 includes a concave portion 30 with a centrally located inlet 32 (as best shown in FIG. 2) facing upwardly and exposed to ambient. The concave portion 30 is adapted to capture and channel a fluid sample containing chemical agents in the form of an aerosol or droplet, and/or liquid aggregates of the aerosol or droplet falling and landing on the collector funnel 16. The slope of the concave portion 30 and the surface coating is selected to enhance aerosol collection efficiency by facilitating the transfer of aerosol droplets into the inlet 32. The slope and coating can be determined experimentally using the chemical or chemicals of interest. Examples of such coatings may include anodized aluminum, polytetrafluoroethylene, diamond, and combinations thereof.

The collection chamber housing 18 further defines an interior cavity 34 (as shown best in FIG. 2) in fluid communication with the inlet 32. The fluid sample flows into the interior cavity 34 of the collection chamber housing 18 through the inlet 32 where the fluid sample is processed into a vaporous form by the heating component 14 prior to sending the vaporized sample to the chemical detection system as will be further described hereinafter. The collection chamber housing 18 may further include drainage holes or vents (not shown) to maintain vapor concentration and prevent water buildup within the device 10.

The collection chamber housing 18 and the collection funnel 16 are heated by the heating component 14 through the cartridge heaters 26. The cartridge heaters 26 are interiorly positioned to supply heat within the collection chamber housing 18. The cartridge heaters 26 are electrically powered by the switching relay 28 through the control unit 22. The user can operate the control unit 22 via the control panel 36 to pre-set the desired temperature of the interior cavity 34 of the collection chamber housing 18. The thermocouple 24 is located in the interior cavity 34, and enables the control unit 22 to maintain the temperature of the collection chamber housing 18 to remain in the desired range. The temperature range selected is the temperature at which the aerosol or droplet form of a chemical warfare agent becomes vaporized.

Figure 3:
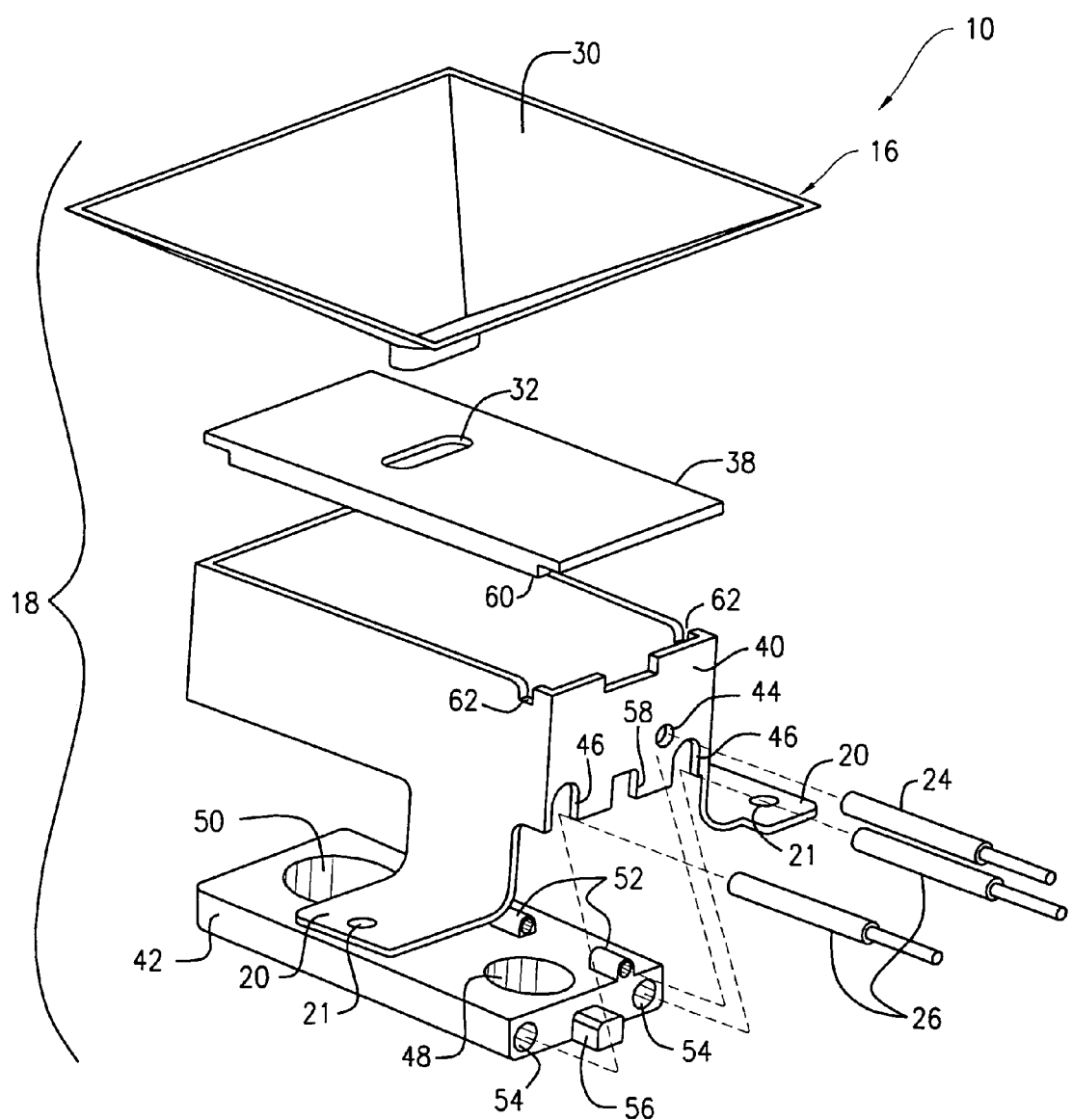
FIG. 3 is an assembly view of the chemical detector aerosol collector in accordance with the present invention.
Figure 5:
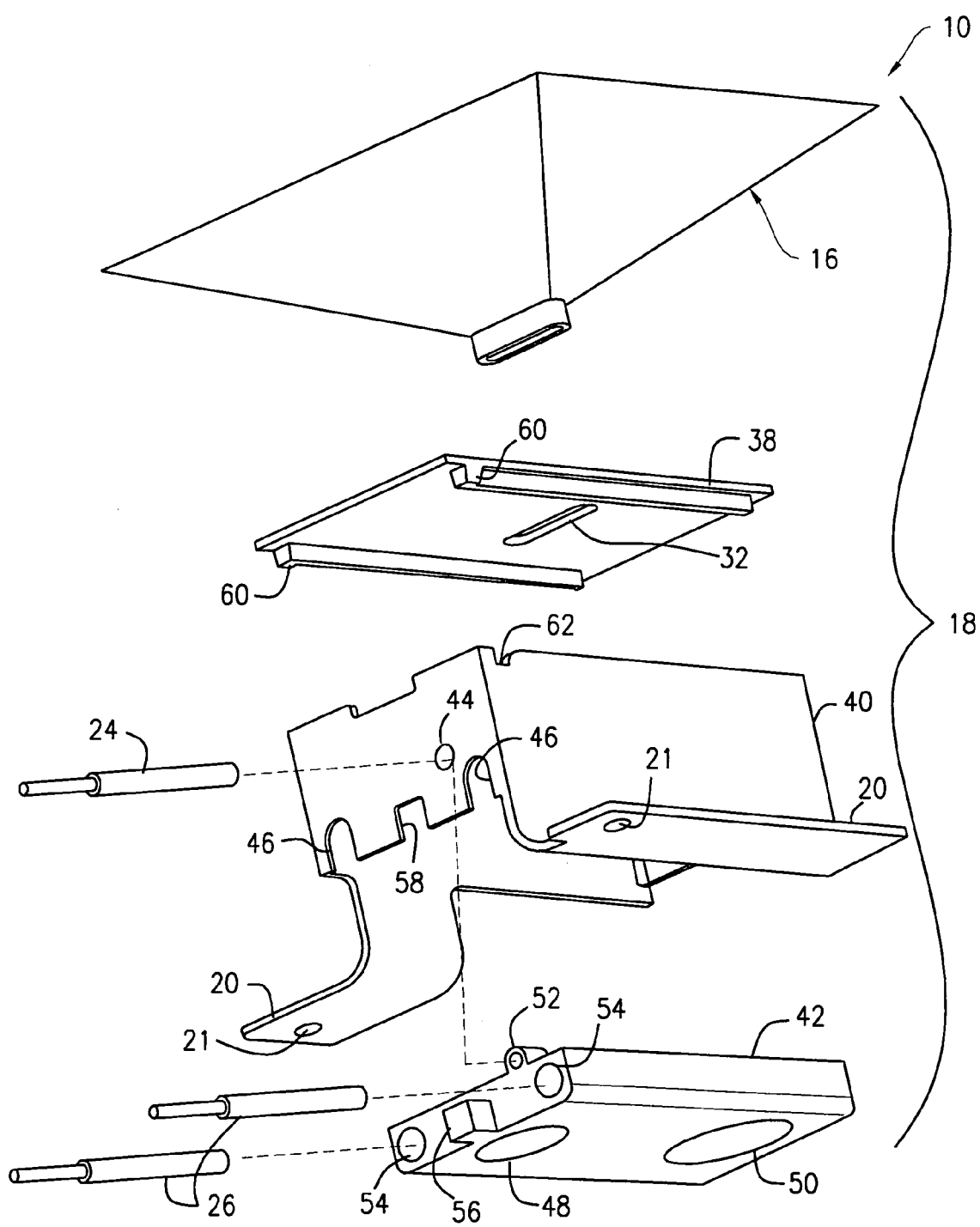
FIG. 5 is an assembly view of the chemical detector aerosol collector in accordance with the present invention.

Referring to FIGS. 2 and 3, the collection chamber housing 18 comprises a top plate portion 38, a mid-housing portion 40 and a base plate portion 42. The top plate portion 38 is configured to accommodate and retain the collection funnel 16. The mid-housing portion 40 includes a thermocouple access hole 44 and cartridge heater access holes 46 for permitting entry of the thermocouple 24 and the cartridge heaters 26, respectively, into the interior cavity 34. The base plate portion 42 includes an outlet 50, a secondary inlet 48, and a pair of mounting brackets 52 for supporting the thermocouple 24 at an elevated position in the interior cavity 34. The base plate portion 42 further includes a pair of longitudinal bores 54 (as best shown in FIGS. 3 and 5) each extending therethrough for receiving and retaining the corresponding cartridge heater 26, and end protrusions 56 each located at the end portions thereof. The end protrusions 56 are shaped to correspond to alignment slots 58 located on the mid-housing portion 40, and ensure the proper alignment and orientation of the base plate portion 42 relative to the mid-housing portion 40 during assembly.

The cartridge heaters 26 operate to heat the collection chamber housing 18, the interior cavity 34 and the collection funnel 16. This allows the fluid sample to be sufficiently heated as it proceeds from the collection 16 to the interior cavity 34. The fluid sample is generally channeled by the funnel 16 along the gas stream flowing through the inlet 32 or along the surface of the concave portion 30 of the collection funnel 16.

The outlet 50 is adapted to be attached to the input port of the chemical vapor detection system. The sample collected by the aerosol collecting device 10 is conveyed for testing through the outlet 50 by low pressure gradient generated by the chemical vapor detection system. The device 10 may be operated with the secondary inlet 48 attached to the output port of the chemical vapor detection system. This generates a continuous gas stream flowing within the interior cavity 34 from the secondary inlet 48 to the outlet 50. The gas stream creates a low pressure gradient across the inlet 32 and draws aerosol or droplet sample therethrough which becomes intermingled with the gas stream.

As the fluid sample is drawn into the interior cavity 34, the aerosol and droplet form of the chemical compound of interest is converted into a vapor in the presence of the elevated temperature in the interior cavity 34. If the aerosol or droplet is larger, it will drop from the gas stream and onto the base plate portion 42 where it is vaporized before it is returned to the gas stream flowing into the chemical vapor detection system. Therefore, this vapor conversion may occur in the gas stream of the interior cavity 34, or upon contact with the base plate portion 42. The collection chamber housing 18 is constructed to define an interior cavity 34 with minimal volume to generate elevated vapor concentration for enhancing detection thresholds. The chamber volume and the operating parameters can be determined experimentally using the chemical or chemicals of interest in order to achieve the optimal detection response time.

Figure 4:
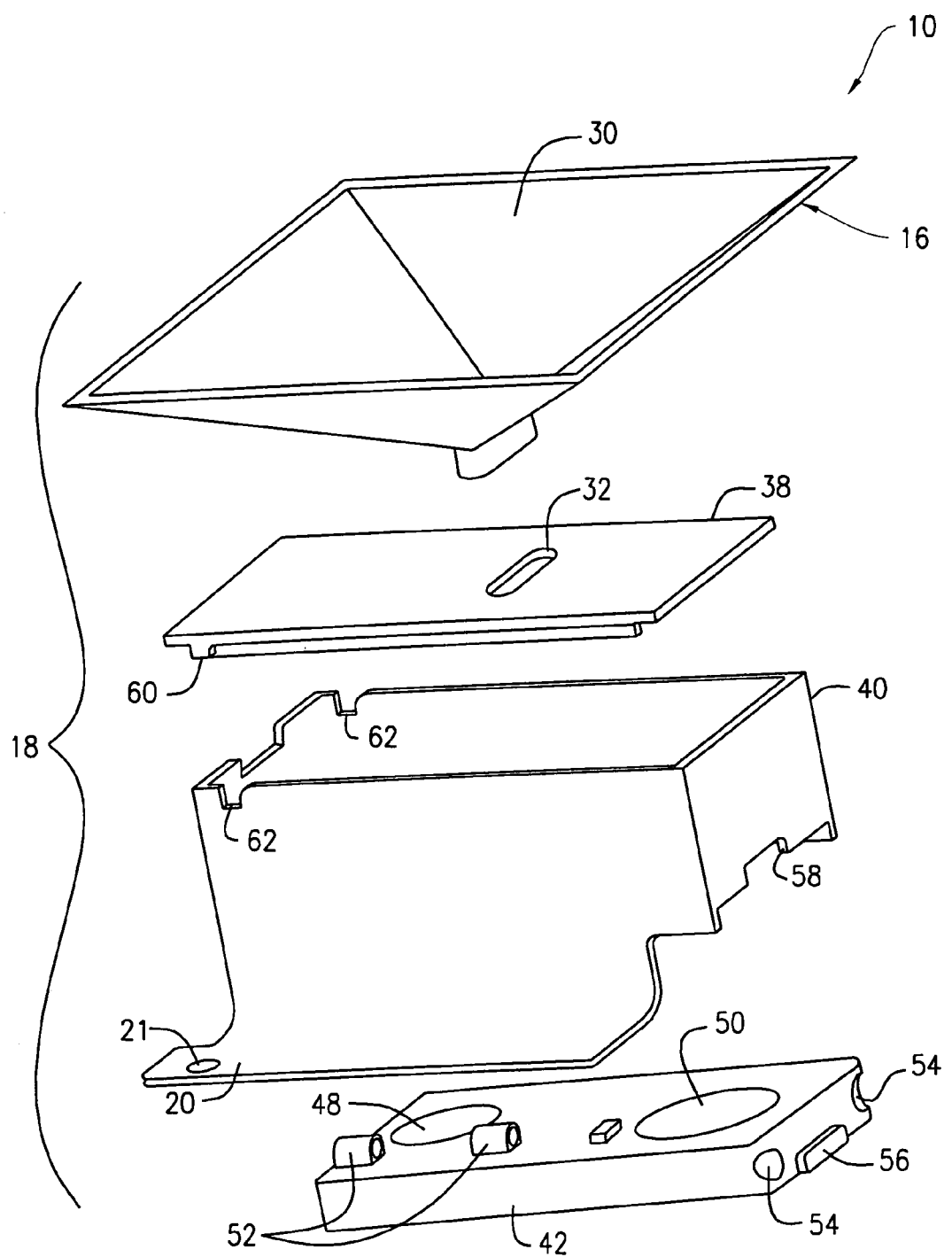
FIG. 4 is an assembly view of the chemical detector aerosol collector from a side opposite from that shown in FIG. 3 without the thermocouple and heating elements in accordance with the present invention.

Referring to FIGS. 3 to 5, the aerosol collecting device 10 is fabricated from multiple discrete members to yield a modular ready-to-assemble construction. The discrete members may be connected to one another through any suitable fastening means including, but not limited to, adhesives, welding, frictional retainment, mechanical clasps, screws, and nuts and bolts. The aerosol collecting device 10 may be adapted for easy disassembly for transport and storage, or assembly into a permanently operational form.

The cartridge heaters 26 are inserted into the longitudinal bores 54, respectively. The base plate portion 42 is inserted into the bottom opening of the mid-housing portion 40 in a slip-fit manner with the end protrusions 56 of the base plate portion 42 occupying the corresponding alignment slots 58 of the mid-housing portion 40, and the exposed portions of the inserted cartridge heaters 26 positioned within the corresponding cartridge heater access holes 46. The thermocouple 24 is inserted through the thermocouple access hole 44 of the mid-housing portion 40 and retained proximate the base plate portion 42 within the interior cavity 34 by the mounting brackets 52. The top plate portion 38 includes tab projections 60 shaped to fit into corresponding slots 62 of the mid-housing portion 40. The top plate portion 38 is inserted into the top opening of the mid-housing portion 40 in a slip-fit manner with the tap projections 60 seated in the corresponding slots 62. The collection funnel 16 is attached to the top plate portion 38 with the lower end of the funnel 16 inserted through the inlet 32 of the top plate portion 38. The assembled aerosol collecting device 10 is coupled to the corresponding chemical vapor detection system with the outlet 50 fluidly connected to the input port of the detection system, and the secondary inlet 48 fluidly connected to the output port of the detection system.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. An aerosol collecting device, comprising:
    a housing adapted for attachment to a chemical vapor detection system, said vapor detection system capable of analyzing a sample suspected of containing a chemical warfare agent, wherein said housing defines a chamber comprising an inlet open to ambient, an outlet, and a through cavity defined therebetween, said outlet being adapted for fluid connection with an input port of the chemical vapor detection system;
    a collecting funnel attached to the inlet for collecting and channeling droplets or aerosol into the inlet, wherein said funnel includes a coating to facilitate transfer of aerosol droplets; and
    a heating element for heating the chamber to a temperature above the boiling point of a target chemical agent of interest, wherein the relevant portion of the sample in the form of a droplet or aerosol which may contain the chemical agent is converted into a vapor form as it passes through the cavity from the inlet to the outlet of the chamber, and prior to entering the input port of the chemical vapor detection system.

2. The aerosol collecting device of claim 1, wherein the inlet and the collecting funnel are located on a top plate portion of said housing.

3. The aerosol collecting device of claim 1, wherein the heating element is located in a base plate portion of said housing opposite from the inlet.

4. The aerosol collecting device of claim 3, wherein the base plate portion is composed of a heat conducting material.

5. The aerosol collecting device of claim 1, wherein the heating element is electrically connected to a temperature control system comprising a thermocouple connected thereto for automatically maintaining the temperature of the chamber within a desired range.

6. The aerosol collecting device of claim 1, further comprising a second inlet adapted for connection to an outlet of the chemical vapor detection system, wherein a corresponding flow stream is generated between the second inlet and the outlet of the chamber.

7. The aerosol collecting device of claim 1, wherein the heating element is located within a wall portion of the housing.

8. The aerosol collecting device of claim 7, wherein the heated wall portion is located opposite from the inlet.

9. The aerosol collecting device of claim 8, wherein the heated wall portion is composed of a heat conductive material.

10. The aerosol collecting device of claim 1, wherein the outlet is axially offset from the inlet.

11. The aerosol collecting device of claim 1, further comprising means for draining the housing of excess fluid accumulated in the chamber.

* * * * *